United States Patent [19]
Webb et al.

[11] Patent Number: 5,568,895
[45] Date of Patent: Oct. 29, 1996

[54] TREATMENT OF WASTE MATERIALS FOR DISPOSAL

[75] Inventors: Stephen Webb; Richard J. Lear, both of Cairns, Australia

[73] Assignee: Matrix Technology Pty. Ltd., Mooroobul, Australia

[21] Appl. No.: 351,366

[22] PCT Filed: Jun. 7, 1993

[86] PCT No.: PCT/AU93/00268

§ 371 Date: Dec. 9, 1994

§ 102(e) Date: Dec. 9, 1994

[87] PCT Pub. No.: WO93/25329

PCT Pub. Date: Dec. 23, 1993

[30] Foreign Application Priority Data

Jun. 9, 1992 [AU] Australia ..................... PL2810

[51] Int. Cl.$^6$ ..................... B02C 9/04; B02C 21/02; B02C 23/18
[52] U.S. Cl. ..................... 241/16; 241/21; 241/29; 241/34; 241/41; 241/101.71; 241/101.8; 241/152.2; 241/606; 241/DIG. 38
[58] Field of Search ..................... 241/16, 21, 29, 241/33, 34, 38, 41, 101.8, 152.2, 236, 606, DIG. 38

[56] References Cited

U.S. PATENT DOCUMENTS

| | | | |
|---|---|---|---|
| 3,506,200 | 4/1970 | Raudenbush | 241/41 |
| 3,547,577 | 12/1970 | Lovercheck | 241/DIG. 38 X |
| 4,149,968 | 4/1979 | Kupiec et al. | 210/28 |
| 4,509,696 | 4/1985 | Donaldson | 241/15 |
| 4,518,508 | 5/1985 | Conner | 210/751 |
| 4,578,185 | 3/1986 | Wilson et al. | 241/606 X |
| 4,884,756 | 12/1989 | Pearson | 241/606 X |
| 4,898,615 | 2/1990 | Vazquez et al. | 106/103 |
| 5,028,010 | 7/1991 | Sansing | 241/101.8 |
| 5,251,825 | 10/1993 | Dumaine et al. | 241/DIG. 38 X |

FOREIGN PATENT DOCUMENTS

| | | |
|---|---|---|
| 2620637 | 9/1987 | France . |
| 2654020 | 11/1989 | France . |
| 3943147 | 12/1989 | Germany . |
| 3943147A | 7/1991 | Germany . |

Primary Examiner—Timothy V. Eley
Attorney, Agent, or Firm—Lowe, Price, LeBlanc & Becker

[57] ABSTRACT

Organic wastes are made suitable for disposal by sequential treatment with an oxidizing solution and an alkaline earth oxide or hydroxide. The treated waste is then mixed with an absorbent material to absorb excess liquid, and optionally with a binding material. An apparatus for carrying out the method comprises a feed hopper, a shredder, mixer and appropriate metering means.

17 Claims, 6 Drawing Sheets

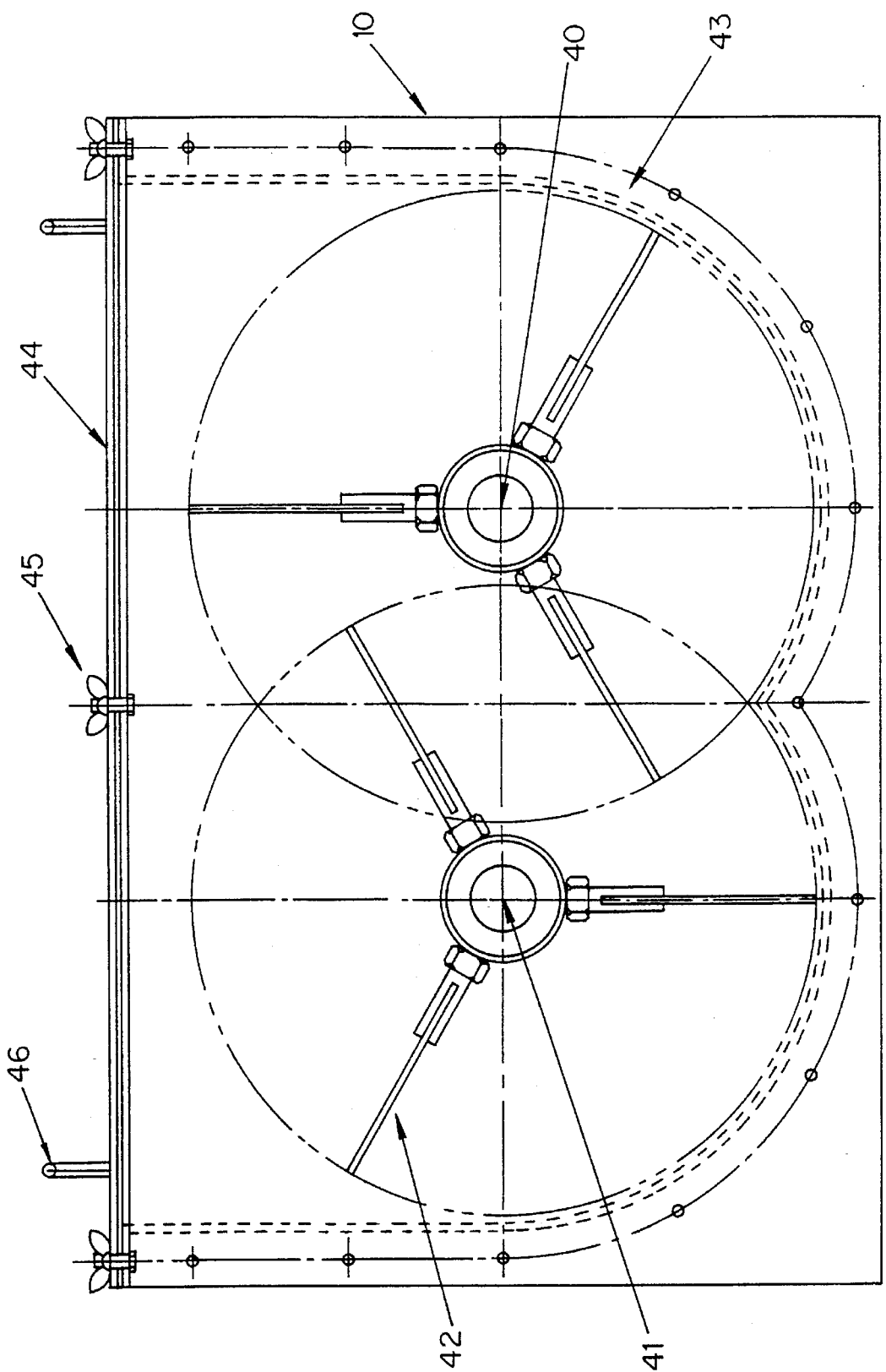

TREATMENT OF WASTE MATERIALS FOR DISPOSAL

TECHNICAL FIELD

This invention is concerned with the disposal of wastes which are or may become biologically active, waste materials including, but not limited to, hospital waste materials comprising clinical waste materials including pathogenic materials, quarantine wastes, sewerage sludges, putrescible food wastes and the like as well as wastes which may contain heavy metals.

BACKGROUND ART

Hitherto the disposal of clinical waste materials has been confined generally to incineration. Apart from being environmentally unacceptable in terms of $CO_2$, CO, NOx, $SO_2$, halogenated hydrocarbon and dioxin emissions, this form of disposal of waste materials has not been proven safe in that average incineration temperatures may not be great enough to destroy biologically active materials present in the clinical wastes. Furthermore, during the start up of an incineration phase, before effective temperatures are reached, there may occur emissions of bacteria and caner microorganisms and pathogenic material generally.

Similarly, disposal of quarantine wastes such as foodstuffs and plant specimens is usually carried out by incineration with the same degree of uncertainty as to the possibility of release of active plant and animal pathogens to the atmosphere.

Sewerage sludges and putrescible organic food waste materials are usually buried in urban land fill sites with significant risk of release c gaseous pathogens to the atmosphere, but, more importantly, it is known that such organic materials decompose to release large quantities of methane gas, a known contributor to the "greenhouse effect".

Apart from incineration or burying in urban landfill sites, there presently exists no known biologically and environmentally safe method of disposal of wastes including organic materials which may include, or generate during decomposition, biologically threatening consequences.

DISCLOSURE OF THE INVENTION

Accordingly, it is an aim of the present invention to overcome or ameliorate the known disadvantages of disposal of waste materials, including pathogenic organisms and to provide a general method for safe disposal of organic wastes.

According to one aspect of the present invention there is provided a method for disposal of waste materials comprising the steps of:

treating waste material with an oxidising solution;

subsequently treating said waste material with an alkaline oxide or hydroxide;

mixing the treated waste material with an absorbent material to absorb excess liquid; and optionally mixing said treated waste material with an effective quantity of a binding material such as alkaline earth silicate to form a solid siliceous mass or a cementitious binder.

Preferably said oxidising solution comprises a source of free oxygen such as ozone, or a peroxide, a source of free halogens or oxy-halogens such as chlorine, hypochlorites or other oxidants including metabisulphates, nitrites, formaldehyde or glutaraldehyde. Most preferably the oxidising solution comprises hydrogen peroxide or peracetic acid.

Suitably said alkaline oxide or hydroxide comprises calcium oxide or hydroxide, potassium or magnesium oxide or, calcium, potassium or magnesium hydroxide or a mixture thereof. Alternatively said alkaline hydroxide may comprise an alkaline earth carbonate or bicarbonate.

The absorbent material may comprise any suitable inert absorbent such as bentonite, silica,, clay minerals such as bauxite, kaolin, mineral ashes, calcines, fly ashes or other mineral residues from industrial processes, siliceous materials such as diatomaceous earths or the like.

According to a second aspect of the invention there is provided an apparatus for carrying out the process according to the invention, said apparatus comprising:

a feed hopper;

a shredding means with an inlet associated with said feed hopper;

a mixing means adapted to receive shredded material from said shredder;

a first metering means to introduce an oxidising solution into said feed hopper as a spray of droplets;

a second metering means to introduce an alkaline earth oxide or hydroxide into said mixing means;

a third metering means to introduce a mineral absorbent into said mixing means;

a fourth metering means to introduce a cementitious binder into said mixing means; and discharge means to discharge treated material from said mixing means.

Preferably said apparatus comprises a hopper feed means.

Suitably said hopper feed means includes means to determine the mass of material to be treated.

The shredding means may comprise any suitable means to reduce a waste material to a particulate form.

If required the shredding means may comprise a two stage shredding apparatus having the output of a first shredder in communication with the input of a second shredder.

Preferably said shredding means comprises counter rotating knives and hooks.

The mixing means suitably comprises a high shear mixer.

Preferably the mixing means comprises a paddle type mixer.

The first, second, third and fourth metering machines are preferably coupled to said hopper feed means to permit feeding at predetermined rates and predetermined ratios of said oxidising solution, said alkaline earth oxide or hydroxide, said mineral absorbent and said cementitious binder respectively.

If required said apparatus may include a fifth metering means coupled to a source of liquid to introduce said liquid to selectively control consistency of treated material.

The discharge means may comprise any suitable conveyor means and if required may include rotary pelletising means.

BRIEF DESCRIPTION OF THE DRAWINGS

In order that the invention may be more fully understood, reference is now made to various preferred embodiments illustrated with reference to the accompanying drawings in which:

FIG. 7 shows a cross sectional view through the mixer of FIGS. 1–3.

DESCRIPTION OF THE INVENTION

Figure 1:
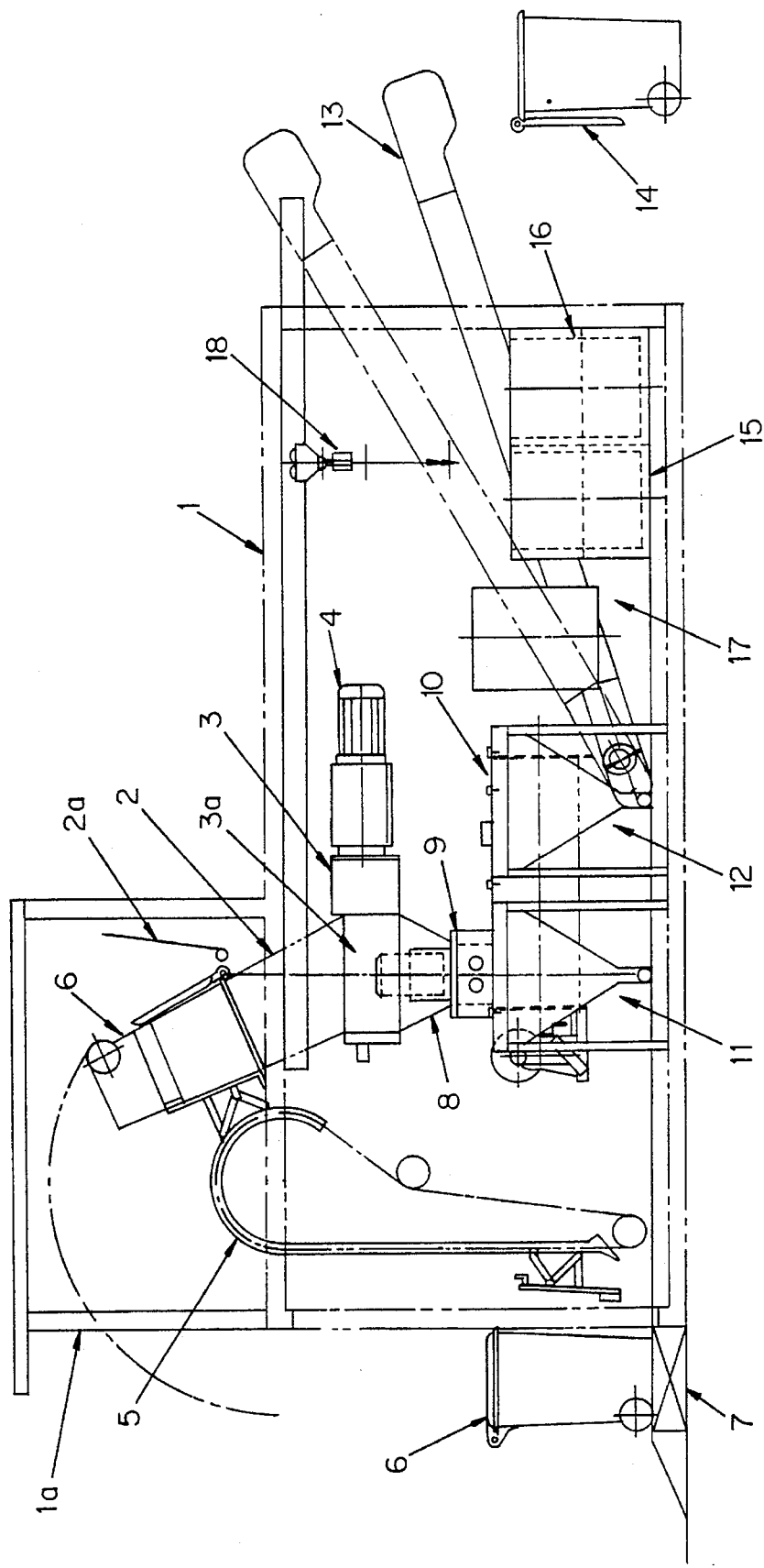
FIG. 1 illustrates a side elevation of an apparatus for processing organic waste materials according to the invention.
Figure 2:
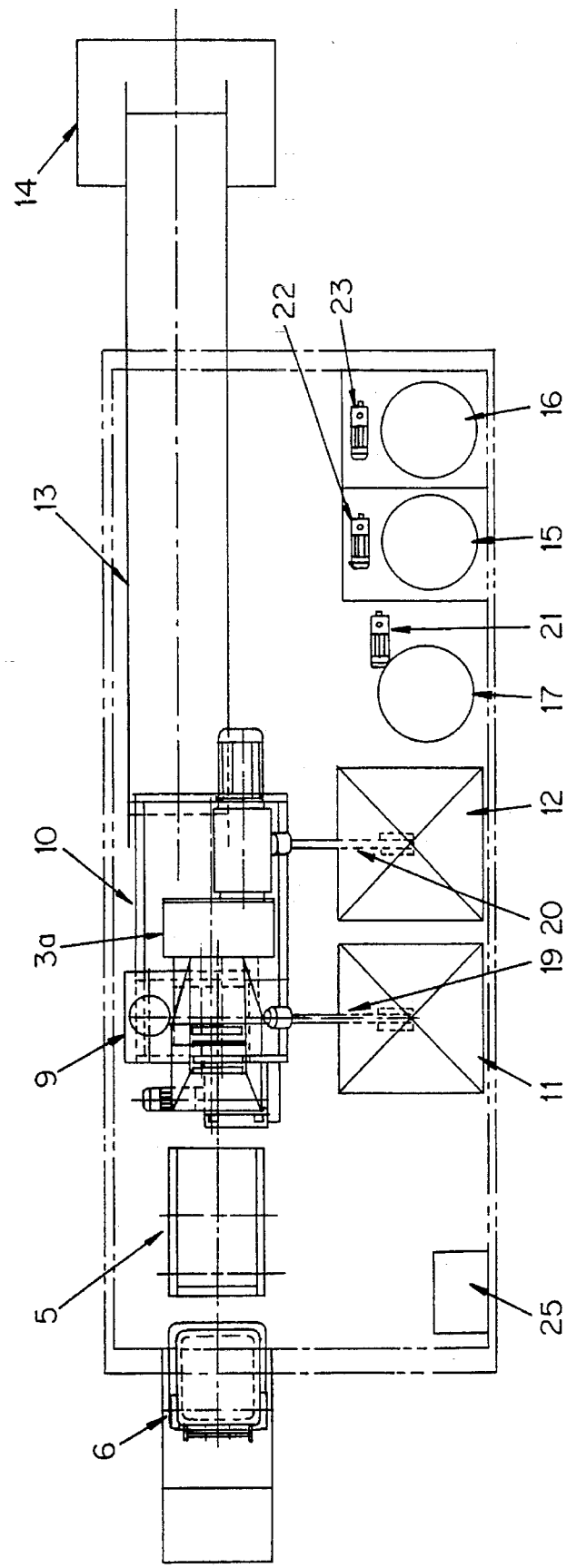
FIG. 2 illustrates a top plan view of the apparatus of FIG. 1.
Figure 3:
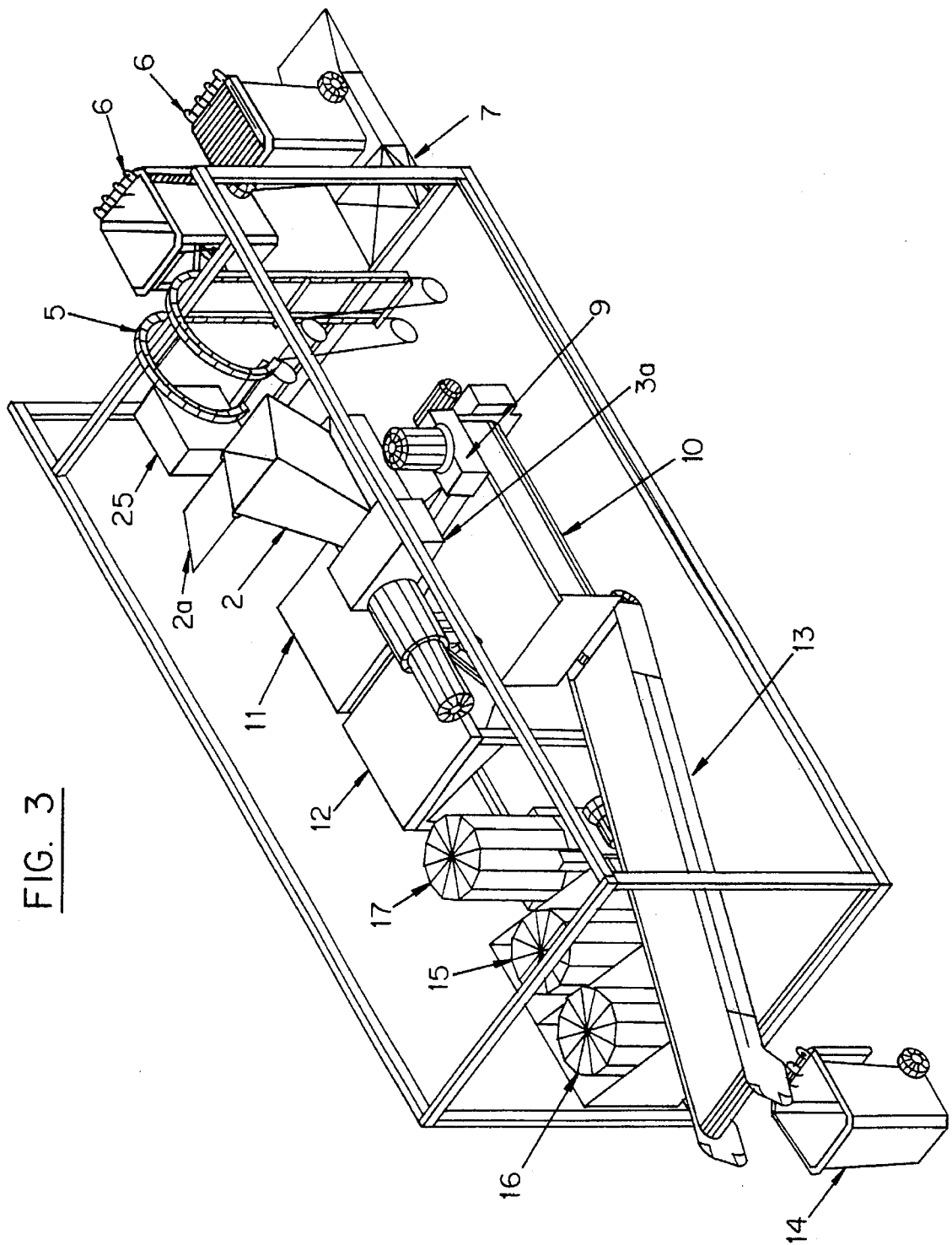
FIG. 3 illustrates a schematic perspective view of the apparatus shown in FIGS. 1 and 2.

In FIGS. 1–3, the apparatus is conveniently located in a housing 1 such as a portable shipping container.

The apparatus comprises a feed hopper 2 associated with a shredding or pulverising apparatus 3 driven by an internal combustion motor or electric motor 4. The feed hopper 2 communicates with an opening in housing 1 and this opening preferably includes a lockable hatch or the like (not shown).

Associated with housing 1 is an elevation mechanism 5 which is adapted to selectively elevate and tip a conventional 250l wheeled refuse bin 6. Bin 6, for the purpose of elevation has a location position on a weighing apparatus 7 such as a load cell platform or the like calibrated to determine the load contained in bin 6.

A conveniently located operation panel (not shown) on the exterior of the housing 1 in the region of bin 6 is provided for authorised operation of the apparatus by means of a key activated switch or the like.

Upon activation of the operation switch associated with the operation panel, bin 6 containing waste materials is elevated and the contents thereof are tipped into hopper 2. Preferably the mouth of container 6 is adapted to sealingly engage the mouth of hopper 2 to ensure no spillage of contents from container 6.

Hopper 2 provides a feed chute for primary shredder 3a, the outlet port of which is in communication with the inlet port or feed hopper 8 of secondary shredder 9.

Feed hopper 2 may comprise a closure door 2a to seal the chute 2 having a shredding operation. Preferably however, the mouth of chute 2 is sealed by leaving bin 6 sealingly engaged with hopper 2 during the shredding process to provide a closure to hopper 2. Hydraulically or pneumatically actuated door 2a is provided to close hopper 2 in the absence of bin 6 forming a closure.

During the tipping of refuse from bin 6 into hopper 2, spray jets (not shown) located within hopper 2 direct an aqueous spray of 1–10% hydrogen peroxide solution or a spray of 0.1–5% of peracetic acid into the hopper 2 to thoroughly wet the waste material being fed into hopper 2.

The wetted refuse then enters the shredding apparatus 3 which preferably comprises a primary shredder 3a and a secondary shredder 9 to ensure that the feed material is reduced to a finely particulate matter. Suitably both primary and secondary shredders 3a and 9 comprise rotary knife and hook shredders such as Brentwood AZ-15 and Brentwood AZ-7 (Trade Mark) shredders respectively. A two stage shredding process is preferred to ensure adequate shredding however other types of shredders may be employed to ensure adequate reduction of the waste feed to a treatable particle size depending upon the nature of the waste. The apparatus described with reference to the preferred embodiment has been trialled with conventional hospital waste comprising fabric bandages, swabs, glass, plastics and even stainless steel surgical implements accidentally included in the waste.

The waste materials, after thorough wetting with an oxidising solution such as 1–10% hydrogen peroxide or peracetic acid containing from 0.1% to 5% $H_2O_2$ are then subjected to "wet" shredding whereby any pathogenic aerosols created during the shredding process are captured by the oxidant spray. If required, the oxidant spray may also be selectively directed into bin 6 to wash out the bin and thoroughly disinfect it.

The shredded or pulverised waste passes from primary shredder 3a to secondary shredder and hence into a high shear mixing apparatus 10.

The shredded oxidised material entering mixer 10 then has added to it calcium oxide (burnt lime) or calcium hydroxide (slaked lime) from hopper 11.

After thorough mixing with the alkaline compound, the treated waste material progresses through the mixer to a point where an absorbent such as bentonite is added from hopper 12 to convert the mixture to a paste like consistency. In the last stage of mixing a cementitious binder such as portland cement, fly ash or preferably aqueous sodium silicate is added before the thoroughly mixed and reacted materials exit from an adjustable opening (not shown in the mixer).

The treated waste with a paste-like consistency is then fed onto conveyor 13 to exit housing 1 in the form of particles or balls of soft clay-like consistency into a collection bin or the like 14. Conveyor 13 may be adjustable in elevation either to assist in "bailing" of the treated waste or to assist in loading of treated waste into a vehicle borne collection bin.

Removable containers of water 17, sodium silicate 15 and hydrogen peroxide 16 are positioned beneath a gantry crane 18 to facilitate removal of empty containers and insertion of filled containers.

FIG. 2 shows a plan view of the apparatus of FIG. 1.

In FIG. 2 flexible screw conveyors or the like 19, 20 are employed to feed particulate calcium oxide and bentonire from hoppers 11, 12 respectively. Metering pumps 21, 22, 23 respectively are employed to feed water, sodium silicate and hydrogen peroxide to their respective feed or introduction points in the system.

A microprocessor or programmable logic controller 26 is provided to control the various aspects of the process such as feed ratios of water, hydrogen peroxide, lime, bentonite, sodium silicate and mixer speed as a function of the feed mass detected by load cell 7. Microprocessor 7 is programmable to compensate for differing types of feed material including moisture content to ensure a thoroughly treated safe material exits from the apparatus for subsequent disposal.

FIG. 3 shows a revealed perspective view of the apparatus of FIG. 1 and 2.

Figure 4:
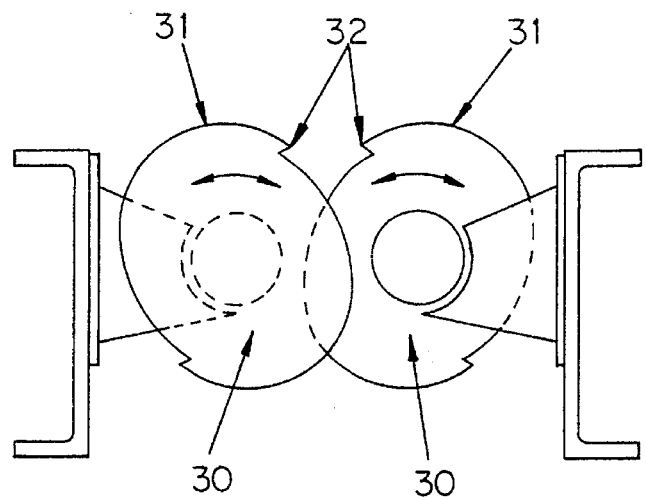
FIG. 4 is an enlarged part cross sectional view of a shredder assembly.

FIG. 4 shows schematically the preferred type of shredding apparatus.

This apparatus comprises parallel rows of alternately spaced cutting blades 30 which contra-rotate to provide a rotary cutting action between sharpened edges 31. In addition, the peripheral edges of blades 30 include hooked projections 32 to assist in the shredding action.

Figure 5:
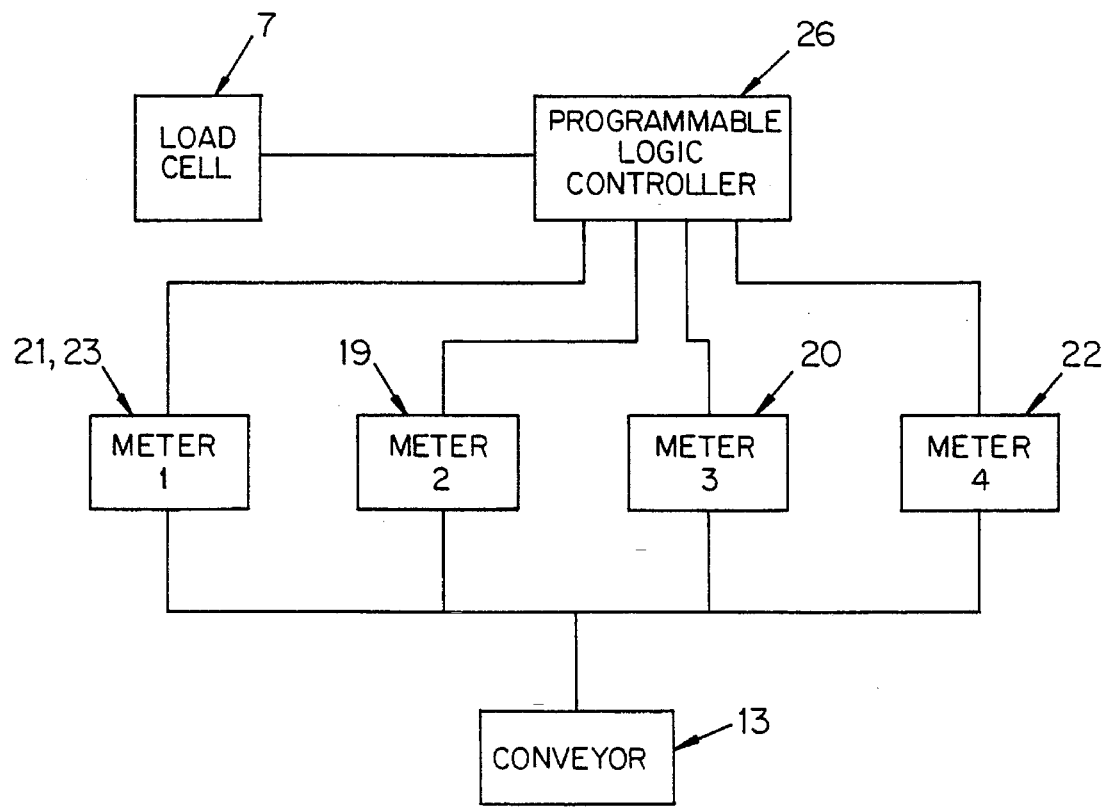
FIG. 5 shows schematically a materials flow chart.

FIG. 5 shows schematically a control circuit from the apparatus of FIGS. 1–3.

As a function of the nett mass of the waste material determined by lead cell 7, programmable logic controller 26 determines, for a predefined waste material type such as hospital waste, the concentration of the oxidant by metering respective sources of 50% $H_2O_2$ and water to obtain say a 5% $H_2O_2$ solution and its feed rate and the mass or volumetric ratios of calcium oxide (burnt lime), bentonite and calcium silicate to obtain a treated waste material in the form of a moist paste of a predetermined consistency. By controlling moisture content, the moist clay like material so produced issues from the high shear mixer 10 in the form of small aggregate particles of 10–20 mm in diameter, larger balls of 20–60 mm in diameter or lumps of paste like material depending upon the preferred form of disposal.

The material so produced may be transported immediately to a land fill site for dumping whereupon the development of a hard cemented material may develop over several days. Alternatively the material may be left to cure for a period of time to harden before dumping occurs.

Figure 6:
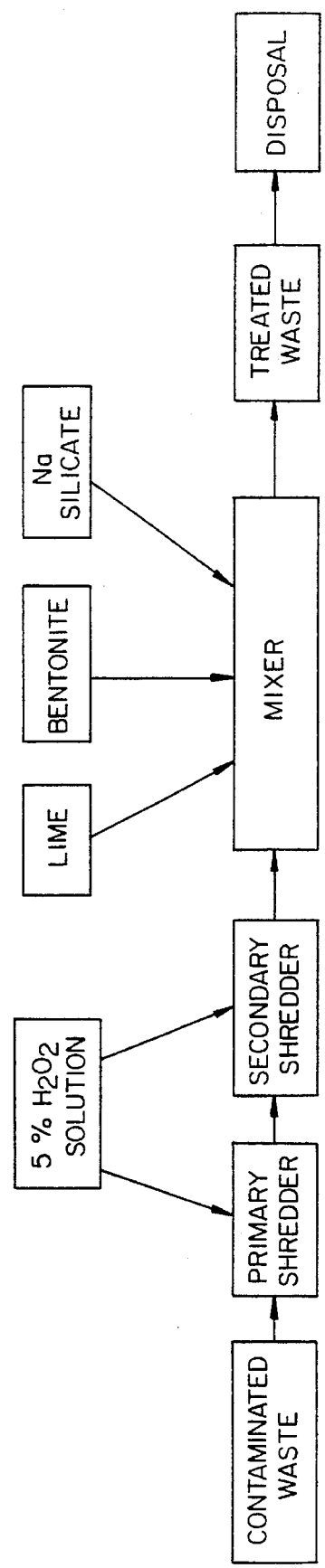
FIG. 6 shows schematically an electrical control circuit for the apparatus of FIGS 1–3.

FIG. 6 shows a schematic flow chart of the process in accordance with the invention.

FIG. 7 shows a cross sectional view of mixer 10.

The mixer 10 comprises contra-rotating shafts 40,41 to which blades 42 are attached. Blades 42 have a fixed or adjustable pitch to convey mixed material from one end of the mixer body 43 to the other at a predetermined rate depending upon the nature of the material to be treated and the treatment duration required to neutralise or deactivate known or suspected microorganisms in the waste material.

A top lid 44 is retained in place by wing nuts 45 or the like and handles 46 are provided to remove lid 44 for cleaning etc. A slidable outlet door (not shown) is provided in the lower front portion of one side of body 43 to selectively control both metering of treated waste and residence time in the mixer. Residence time may also be controlled by the pitch of blades 42 and/or rotational speed of shafts 40, 41.

Preferably one of shafts 40, 41 rotates at a rate greater than the other to increase the mixing shear rate.

During the shredding and pulverising operation metered quantities of water and concentrated hydrogen peroxide (50%) are mixed and fed into the hopper 6 at a 5% concentration to reduce dust and to maintain a required degree of moisture in the shredded waste. Dilute hydrogen peroxide solution is added to the hopper to assist in the moistening of the waste and to commence its oxidation process in the presence of a high shear shredding or maceration process.

The shredded/moistened waste is then introduced to a paddle mixer/conveyor 10 wherein the oxidising process continues.

After a predetermined period of mixing in paddle mixer 10, a quantity of calcium hydroxide is introduced into the paddle mixer/conveyor 10 from container 11 via an appropriate metering means 19.

The mixture of waste material with added oxidant and alkaline earth adjuvant is then further thoroughly mixed in the mixer/conveyer 10 and then a quantity of bentonite or other clay or siliceous absorbent is added from container 12 by a suitable metering means 20 to absorb any excess fluid in the mix.

After thorough mixing of the waste material with the oxidising agent, its oxidising synergist, and the absorbent material, the treated waste is either then deposited in a container 14 for removal or, alternatively treated with an alkaline earth silicate such as sodium silicate delivered as an aqueous solution from container 15 via a suitable metering means 22.

Preferably the apparatus shown in FIGS 1–3 comprises a portable, self contained waste treatment apparatus with predetermined quantities of treatment materials to treat and ultimately store a predetermined quantity of waste material of a predetermined type. The apparatus is suitably controlled by a microprocessor or programmable logic controller 26 coupled to the various metering devices. Control of metering can be effected by various sensors such as a redox potentiometer to measure the degree of oxidation of the waste, moisture sensing devices etc.

After treatment of a predetermined quantity of waste material the entire portable structure may be removed from a collection site to a transfer station and the waste storage bins or containers 6 are removed to a land site fill. Empty or part empty treatment chemical storage containers may be refilled at the transfer station. Alternatively, containers of treated waste may be removed from the collection site and the chemical storage containers are replenished on site.

By making the treatment/storage apparatus totally self contained, the risks of contamination to the public are largely minimised as is the risk of malfunction due to tampering. Where an external storage container is necessitated, the container is suitably coupled to the housing 1 in such a manner as to prevent unauthorised removal and/or tampering.

The present invention is considered to be unique in that while it has been known to denature clinical wastes by oxidation with halogens and oxy-halogens, such treated waste was still incinerated or otherwise transferred to a land fill dump without adequate monitoring or consideration to environmental issues such as ground water leaching or contribution to the "greenhouse effect" through methane generation, gaseous or water soluble halogenated organic compounds or the like.

By sharp contrast, the present invention provides a method of effectively denaturing pathogenic materials including putrescible organic wastes or otherwise deactivating waste material such as sewerage sludges in such a manner that they may be introduced to a land fill dump site in a safe manner, while simultaneously binding any heavy metals in the waste to prevent ground water leaching of any undesirable water soluble materials.

In the case of less risky organic wastes such as quarantine waste (eg. foodstuffs and plant material), the treated organic waste may be safely disposed of in a land fill site without the need to encapsulate the waste in a non-leachable binder.

In the case of pathogenic waste materials from hospital or clinical sources, the treated waste material is preferably treated with the addition of liquid binder such as sodium silicate, which reacts with the alkaline earth oxide such as calcium oxide, calcium hydroxide or the like to form a highly stable inorganic mass encapsulating the organic waste material. The stability of the inorganic binder ensures that ground water leaching of pathogenic or the undesirable materials such as heavy metals is substantially eliminated.

The following examples serve to illustrate the various aspect of the invention.

EXAMPLE 1

Utilising the apparatus illustrated in FIGS. 1–3, clinical waste in the form of swabs bandages, tissue samples, biopsy samples, syringes, drug containers and the like are introduced into shredder or pulveriser 3 to reduce the waste into a particle size of 20 mm or less. At the same time, aqueous hydrogen peroxide at a concentration of from about 2–10% is introduced into the shredder as a spray to wet the shredded mass and to prevent the generation of aerosols which could carry toxic matter.

The shredded, initially oxidised material then drops into the paddle mixer/conveyor 10 whereupon a quantity of calcium oxide or calcium hydroxide is added to synergise the oxidation of the organic waste material by the principal oxidising agent, hydrogen peroxide, or peracetic acid.

After a suitable mixing period, bentonite is added at a rate of from 5–15 kg/m2 of waste material in a quantity sufficient to absorb excess moisture from the treated mass to create a paste like consistency.

Thereafter, depending on the nature of the organic material to be treated, a quantity of sodium silicate in the form of a 5–50% aqueous solution is added to the mass and intimately mixed therewith to form, on standing, a solid, insoluble lime/silicate matrix which may then be safely disposed of in a conventional urban land fill dump site.

EXAMPLE 2

In an initial series of tests a mixture of cat food (primarily meat and fish meal) was mixed with cat biscuits (a source of carbohydrate and protein).

To this putrescible organic material was added:

Hydrogen peroxide: 0.1%–15%

Calcium Oxide: 1%–20% and:various mixtures of bentonite and sodium silicate.

The samples so produced were thoroughly mixed and allowed to rest in a container at ambient conditions to measure the rate of deterioration by the rate of development of bacterial colonies on the surface of the samples.

Compared with the untreated trial sample (allowing for included preservatives, antioxidants etc) some growth of bacterial colonies was observed with a sample treated alone either with $H_2O_2$ (less than 3%) or CaO (less than 5%). However a sample treated with a mixture of 1% $H_2O_2$ and 5% CaO showed no signs of bacterial growth after two weeks under similar conditions.

Of the various samples tested, it was considered that varying fat contents of the meat and fish meal may have contributed to the formation of fatty acid soaps thus affecting the expected solidification of calcium silicate matrices to bind the material in a solid "rock-like" mass resistant to aqueous leaching.

EXAMPLE 3

A putrescent mass of meat, sugar and water was treated sequentially by (i) oxidation with hydrogen peroxide; and then, (ii) alkalinisation with calcium oxide.

A liquid sample of the treated material was then used to inoculate an agar medium.

After two days at 35° C. a white powdery growth was noted in the inoculated site. Monitoring was continued for several days and after the area of inoculated site had remained static after two days, an inorganic contamination was suspected. The white powdery growth was treated with dilute acetic acid to obtain an effervescence which suggested that the "growth" was in fact a deposit of calcium carbonate.

After washing with water the inoculated region of the agar culture medium remained free of any bacterial growth, however it was noted that bacterial growth subsequently occurred in other regions of the agar plate.

EXAMPLE 4

An independent test was carried out by a suitably qualified laboratory on a mixed sample of hospital waste material treated in accordance with the invention and solidified by the addition of sodium silicate.

The solid sample was first swabbed and plate out on nutrient agar.

A 2 gm sample of the solid material was then ground and allowed to remain in sterile water for a period of time. The body of water containing the ground sample was then filtered through a 0.45 micron filter and the filter was placed on membrane faecal coliform agar and incubated for 24 hours.

Except for the control sample none of the tests carried out were positive for pathogenic bacteria ,thereby suggesting the effectiveness of the process according to the invention.

EXAMPLE 5

In order to illustrate the efficacy of the process, a mixture of biomedical hospital waste and fresh horse manure was chosen as a rich and diverse source of microorganisms. The hospital waste comprises a mixture of cotton wool swabs, cotton gauze bandages, plastic bags, plastic containers and the like. The results obtained from various mixtures are set forth in Table 1 below:

TABLE 1

| SAMPLE NO. | FEED | ADDITIVES | Bacteria/gram |
|---|---|---|---|
| 1 | Horse manure untreated | — | $10^{10}$ |
| 2 | 80% w/w hospital waste 20% w/w fresh horse manure | — | TNTC (too numerous to count) |
| 3 | 80% w/w hospital waste 20% w/w fresh horse manure | 15% w/w slaked lime | $6 \times 10^4$ |
| 4 | 80% w/w hospital waste 20% w/w fresh horse manure | 15% w/w slaked lime | $6 \times 10^4$ |
| 5 | 80% w/w hospital waste 20% w/w fresh horse manure | 15% w/w slaked lime | $6 \times 10^4$ |
| 6 | 80 w/w hospital waste 20% w/w fresh horse manure | 15% w/w slaked lime | $24 \times 10^2$ |
| 7 | 80% w/w hospital waste 20% w/w fresh horse manure | 15% w/w slaked lime | $6 \times 10^3$ |
| 8 | 80% w/w hospital waste 20% w/w fresh horse manure | 15% w/w slaked lime | $25 \times 10^3$ |
| 9 | Horse manure alone | 15% w/w slaked lime bentonite | $25 \times 10^3$ |
| 10 | Horse manure alone | 15% w/w slaked lime bentonite, Na Silicate | $25 \times 10^3$ |
| 11 | Horse manure alone | 30% w/w slaked lime | $5 \times 10^2$ |
| 12 | Horse manure alone | 45% w/w slaked lime | $5 \times 10^2$ |
| 13 | Horse manure alone | 30% w/w slaked lime | $10^3$ |
| 14 | Horse manure alone | 60% w/w slaked lime | $17 \times 10^2$ |
| 15 | Horse manure | 12% chlorine | 0 |

TABLE 1-continued

DISINFECTION TRIALS

| SAMPLE NO. | FEED | ADDITIVES | Bacteria/ gram |
|---|---|---|---|
| | | solution | |
| 16 | Horse manure microwaved | — | TNTC |
| 17 | Horse manure boiled | — | 0 |
| 18 | Horse manure | 15% w/w slaked lime | $10^3$ |
| 19 | sample bottle (control) | — | 0 |

Sample 1, comprising untreated horse manure, was dissolved into 5 ml of saline solution and then sub-sampled twice more into saline solution before being plated out to obtain an approximate bacterial count using blood agar.

Samples 2, 3 and 4 were tested immediately after treatment whereas samples 5 and 6 were treated after allowing pelletised treated waste material to sit for four days at ambient temperature conditions.

Sample 18 was a 65 mm diameter ball of treated waste material which was allowed to harden for one week, then was crushed and sampled for bacteria.

All samples tested for the presence of bacteria were dissolved in saline solution and plated out (after vigorous mixing) using a 10 ml loop.

For samples derived from treated materials, bacterial colonies which did develop on agar plates were frequently stunted and atypical in gross appearance.

All samples were tested on both blood agar and McCoupey's agar to obtain counts for bacteria per plate and these figures were extrapolated to bacteria/gram.

From these trials it was concluded that samples treated with hydrogen peroxide and as low as 15% w/w slaked lime showed an immediate disinfection level of 99% and if the waste material was again sampled after several days standing, bacterial activity was reduced to about one tenth of that detected immediately after treatment.

EXAMPLE 6

To further illustrate the effectiveness of the process and apparatus, hospital waste was inoculated with *Pseudomonas aeruginosa* and *Escherichia coli* representing respectively very robust and ubiquitous bacterial species.

In five kilogram bags of hospital waste containing typically, cotton swabs, cotton bandages, items of bed linen, plastics containers, syringes and other materials were fist autoclaved for 30 minutes at 115° C. to ensure complete sterility.

Each of the bags of waste was then inoculated (after cooling) with aqueous solutions containing *Pseudomonas aeruginosa and Escherichia coli*. Before treatment, each bag of waste recorded a colonisation at a rate of $10^8$ bacteria/gram.

In the apparatus shown in FIGS. 1–3 of the drawings the bags of waste were then processed using a 5% hydrogen peroxide solution in the hopper and 25% w/w calcium oxide only. (no bentonite or sodium silicate was added for these tests). With a cycle time of about 4 minutes in the mixer the treated material was found to be about 45° C.–50° C. upon exit from the mixer.

On all ten samples tested after 1 hour and after 24 hours, plated washings of the samples revealed no bacteria whatsoever ie. zero bacteria/gram.

In treatment of infected materials "sterilisation" is taken to be achieved when a reduction of $10^4$ bacteria/gram is obtained.

Accordingly from the foregoing examples it can be seen that the process far exceeds the acceptable standards required for sterilisation of waste materials.

A typical operational sequence for the apparatus shown in FIGS 1–3 is described below.
1. Activate power switch.
2. An extraction fan located within the apparatus and coupled to a biological filter is activated to cause a negative air pressure within the housing.
3. Mixer outlet port closes.
4. Wheeled container placed on load cell - nett mass of contents determined.
5. Container elevated to shredder feed hopper and peroxide sprays initiated as feed enters hopper.
6. Mixer, shredders and elevator activated.
7. After about 5 seconds the screw conveyor attached to the lime hopper is activated.
8. After about 10 seconds bentonite addition to the mixer is commenced.
9. After about four minutes mixing silicate is added to the mixer.
10. After a further period of mixing for about 1 minute the mixer door opens to allow pellets of paste like treated material to fall onto the conveyor belt to exit the housing.

For a typical hospital waste material, its bulk density is about 0.1 mkg/l. For shredded dry waste the bulk density increase to 0.3 kg/l but treated product has a bulk density of about 1 kg/l due mainly to the addition of water.

Three consistencies of treated waste have been produced according to the invention. These include a large block of compressed paste like material which hardens slowly over several days, pellets of an aggregate like material which harden over several hours and a damp loose particulate material comprising shredded waste coated with a mixture of the treatment additives.

Pelletised material can also be formed by means of a drum or other rotary pelletising apparatus.

Typical compositions and flow rates for block, pelletised and granular materials are as follows:

| INGREDIENT | BLOCK | PELLETS | GRANULAR | FEED RATE |
|---|---|---|---|---|
| Dry hospital waste | 100 | 100 | 100 | 200 kg/min |
| Water | 150 | 150 | 150 | (Much in fee) |
| $H_2O_2$ 5% | 50 | 50 | 50 | 10 l/min |
| Slaked lime | 10 | 10 | 10 | 4 kg/min |
| or Quicklime | 15 | 15 | 15 | 3 kg/min |
| Bentonite | 15 | 20 | 10 | 2 kg/min |
| No Silicate (20%) | 10 | 35 | 10 | 2 l/min |

When slaked lime is used, the various exothermic chemical reactions in the mixture give rise to a mixture temperature of between about 30°–35° C. whereas with quicklime, the product temperature can rise as high as 50° C.–60° C. The high mixing temperatures contribute substantially to the destruction of heat labile microorganisms including bacteria, viruses, fungi, protozoans, helminthic parasites and their ova. The neutral pH oxidation process followed by alkaline oxidation is found to be effective in the destruction of more heat resistant micro-organisms such as *Bacillus, subtilis, Candida-albicans, Escherichia-coli, Pseudomonas aeruginosa, Staphylococcus aureus* etc.

More importantly however the combined effects of heat, neutral pH oxidation and alkaline oxidation are considered to provide an amplified if not synergistic biocidal effect.

For the apparatus illustrated in FIGS. 1–3, the lime and bentonire hoppers typically may have a capacity of 500 kg each and the containers for water and the $H_2O_2$ and sodium silicate solution each have a capacity of between 200–250 l. The water container is connected via a flexible hose to a mains source and includes a float valve to maintain its level.

Table 2 shows typical materials consumption rates for the apparatus using a feed which comprised about 15% water content as received in plastic bags from a hospital waste processing centre.

TABLE 2

| MATERIAL | CONSUMPTION/MIN |
|---|---|
| Feed (15% moisture) | 20 kg |
| $H_2O_2$ 2% | 8.5 L |
| | Range 6–12 L |
| Water | 22 L |
| Lime (Ca(OH)$_2$) | 2 kg |
| | Range 1–4 kg |
| Bentonite | 2 kg |
| | Range 1–5 kg |
| Sodium Silicate | 1 L |
| | Range 0.2 L |

In the treatment of hospital waste, it is not common to analyse or identify the type and quantity of microorganisms in untreated waste-rather the effectiveness of a treatment process is determined by simply identifying the presence or absence of microorganisms in the treated waste material. Accordingly there exists no information on a "typical" profile of microorganism populations in a conventional hospital waste stream.

It can however be predicted that a "typical" hospital waste stream may include many of the microorganisms normally associated with healthy human hosts as well as microorganisms associated with diseased persons.

The range of microorganisms may include for example:

Bacteria such as: Camphylobacter, Pseuodomonas, Legionella, Neisseria, Rhizobium, Escherichia, Salmonella, Shigella, Klebsellia, Enterobacter, Bacteroides, Fusobacterium, Rickettsia, Chlamydia, Mycoplasma, Staphylococcus, Streptococcus, Bacillus, Clostridium and Listeria.

These genera represent a wide cross section of aerobic, non aerobic gram positive and spore forming bacteria.

Other microorganisms such as *Candida albicans, Aspergillus* and *Pneumocystis fungi*, protozoa and helminthic parasites can also be found in hospital waste.

There are many chemical disinfectants available for treatment of material containing pathogenic microorganisms. Of these, some are more effective than others and many are effective against certain types of microorganisms only.

The major problem with chemical disinfectants is cost relative to efficacy. While some disinfectants such as sodium or calcium hypochlorite are relatively inexpensive compared to their effectiveness, they are notoriously corrosive in many environments.

Similarly, while heat treatment will effectively sterilise some microorganisms, others are quite resistant.

Accordingly high temperature incineration, despite its pollution problems, has been generally the best compromise between cost and effectiveness in treating hospital waste containing pathogenic microorganisms.

It will be readily appreciated by a skilled addressee that the apparatus and method according to the invention provides an effective, economic means for treatment of wastes containing pathogenic organisms. The chemical treatment processes are simple and easy to manage and the self contained apparatus are virtually fail safe in terms of operation.

None of the chemical residues in the treated product pose any short or long term environmental threat, thus permitting simple and inexpensive disposal in land fill sites.

We claim:

1. A method for treatment of waste materials comprising the steps of:

shredding a waste material to obtain a finely divided particulate material;

wetting said waste material with an oxidizing solution;

to said shredding and wetting steps treating said waste material with an alkaline earth oxide or hydroxide; and mixing the alkaline earth oxide or hydroxide treated waste material with an absorbent material to absorb excess liquid, the resultant treated waste material comprising a moist particulate disinfected mass.

2. A method as claimed in claim 1 wherein the resultant moist particulate mass is further treated with a cementitious binder.

3. A method as claimed in claim 2 wherein the cementitious binder comprises portland cement, fly ash or alkaline earth silicate.

4. A method as claimed in claim 1 wherein said alkaline earth oxide comprises calcium or magnesium oxide.

5. A method as claimed in claim 1 wherein said alkaline earth hydroxide comprises calcium or magnesium hydroxide.

6. A method as claimed in claim 1 wherein the absorbent material comprises a siliceous mineral compound.

7. A method as claimed in claim 1 wherein the oxidising solution comprises an aqueous peroxide solution.

8. A method as claimed in claim 7 wherein the oxidising solution comprises aqueous hydrogen peroxide.

9. An apparatus comprising:

a feed hopper;

a shredding system with an inlet associated with said feed hopper;

a mixer adapted to receive shredded material from said shredder;

a first metering system to introduce an oxidizing solution into said feed hopper as a spray of droplets;

a second metering system to introduce an alkaline earth oxide or hydroxide into said mixer;

a third metering system to introduce a mineral absorbent into said mixer; and, discharge means to discharge treated material from said mixer.

10. An apparatus as claimed in claim 9 including a further metering means to introduce a cementitious binder into said mixing means.

11. An apparatus as claimed in claim 9 wherein the shredding system comprises a primary and secondary shredder.

12. An apparatus as claimed in claim 9 wherein said mixer comprises a high shear mixer.

13. An apparatus as claimed in claim 12 wherein said high shear mixer comprises a paddle mixer.

14. An apparatus as claimed in claim 9 including weighing systems to determine the mass of waste material to be treated.

15. An apparatus as claimed in claim 9 including respective metering systems to selectively introduce said oxidant solution, said alkaline earth oxide or hydroxide, said mineral absorbent and said cementitious binder at predetermined rates.

16. An apparatus as claimed in claim 15 including a weighing system to determine the mass of waste material to be treated and a microprocessor control system coupled to said weighing system and said respective metering systems to selectively control respective ratios of waste material, oxidizing solution, alkaline earth oxide or hydroxide, mineral absorbent and cementitious binder.

17. A portable, self contained waste treatment apparatus comprising:

a feed hopper;

a shredding system with an inlet associated with said feed hopper;

a mixer adapted to receive shredded material from said shredder;

a first metering system to introduce an oxidizing solution to said feed hopper as a spray of droplets;

a second metering system to introduce an alkaline earth oxide or hydroxide into aid mixer;

a third metering system to introduce a mineral absorbent into said mixer;

a weighing system to determine the mass of waste material to be treated;

discharge means to discharge treated material from said mixer; and a microprocessor control system coupled to said weighing system and said respective metering systems to selectively control respective ratios of waste material, oxidizing solution, alkaline earth oxide or hydroxide and mineral absorbent.

\* \* \* \* \*